United States Patent [19]

Adelson

[11] Patent Number: 5,006,722
[45] Date of Patent: Apr. 9, 1991

[54] FLAW ANNUNCIATOR WITH A CONTROLLABLE DISPLAY MEANS FOR AN AUTOMATIC INSPECTION SYSTEM

[75] Inventor: Alexander Adelson, Peekskill, N.Y.
[73] Assignee: Intec Corp., Trumbull, Conn.
[21] Appl. No.: 487,570
[22] Filed: Mar. 2, 1990
[51] Int. Cl.⁵ .................... G01N 21/88; G09G 1/28
[52] U.S. Cl. ..................... 250/563; 340/703; 356/430
[58] Field of Search ............... 250/572, 571, 563, 562, 250/559, 223 R, 226, 221, 222.1; 364/518, 521; 340/701–704, 715; 358/106; 356/429–431, 237–240

[56] References Cited

U.S. PATENT DOCUMENTS

| | | | |
|---|---|---|---|
| 3,887,762 | 6/1975 | Uno et al. | 358/106 |
| 4,044,227 | 8/1977 | Holm et al. | 250/568 |
| 4,439,730 | 3/1984 | Kauffman | 340/703 |
| 4,748,335 | 5/1988 | Lindow et al. | 250/572 |
| 4,776,692 | 10/1988 | Kalawsky | 356/239 |
| 4,824,250 | 4/1989 | Newman | 73/588 |
| 4,910,593 | 3/1990 | Weil | 356/369 |
| 4,933,567 | 6/1990 | Silva et al. | 250/572 |

Primary Examiner—David C. Nelms
Assistant Examiner—Michael Messinger
Attorney, Agent, or Firm—Sprung Horn Kramer & Woods

[57] ABSTRACT

An annunciator system and method for indicating when the number of detected flaws in a moving web is greater than a preselected threshold. The method and system includes a controllable display comprising a matrix of areas each corresponding to one type of the plurality of flaws and each capable of displaying any one of a first, second and third color. Signals corresponding to different detected flaws are received for controlling the display to initially display all of the areas in the first color, to individually change the color of an area to the second color in response to the detection of a first preselected threshold value of flaws of a type corresponding to the area and to individually change the color of an area from the second color to the third color in response to the detection of a second preselected threshold value of corresponding type flaws, which is higher than the first preselected threshold value.

10 Claims, 3 Drawing Sheets

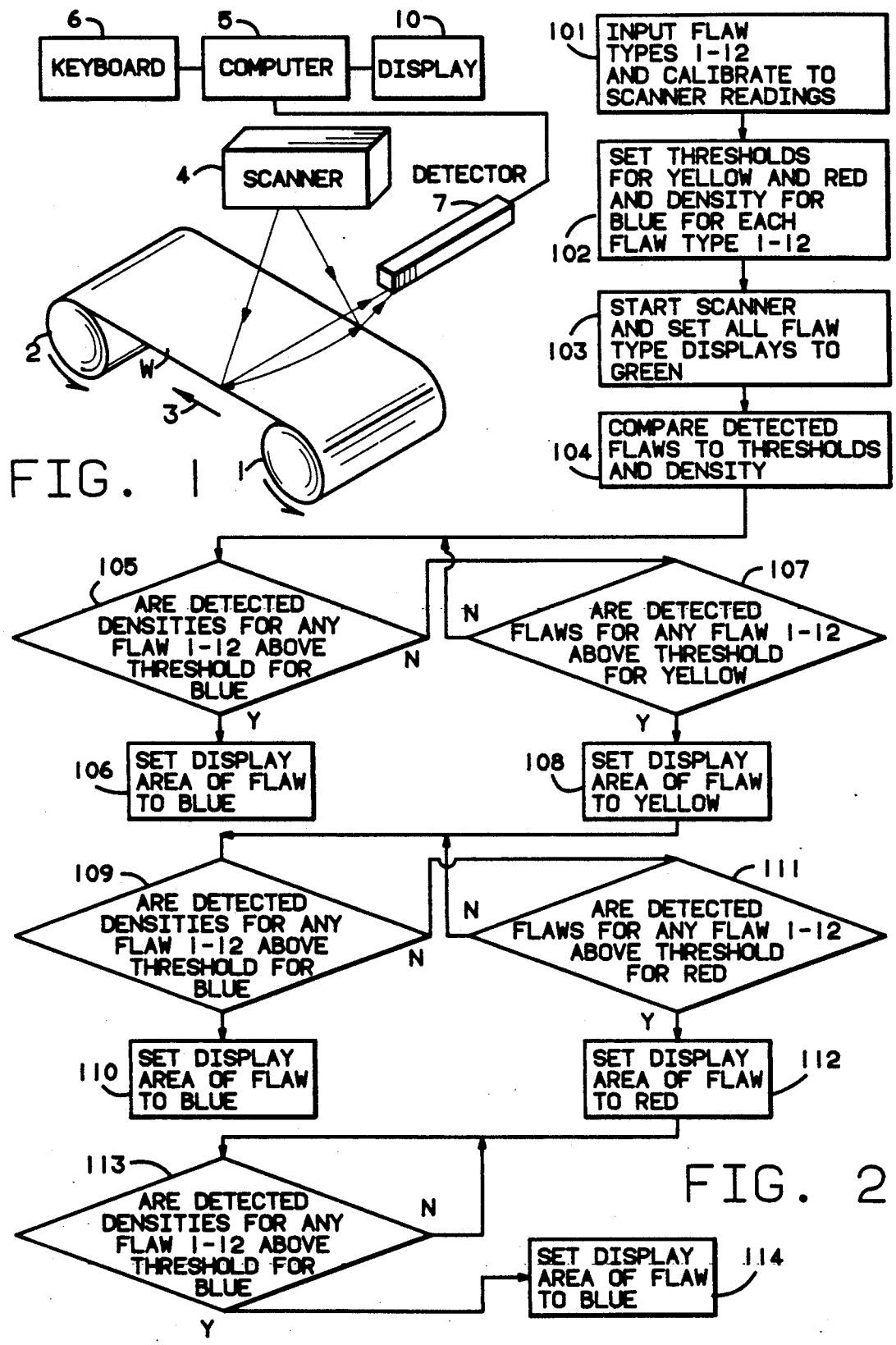

FLAW ANNUNCIATOR WITH A CONTROLLABLE DISPLAY MEANS FOR AN AUTOMATIC INSPECTION SYSTEM

BACKGROUND OF THE INVENTION

The present invention relates to an automatic inspection system including a scanning apparatus for the detection of flaws on a moving web of material and in particular to a method and system for displaying detected flaws.

Flaw detection systems are known in the prior art, as disclosed in U.S. Pat. No. 4,265,545. The prior art systems discussed in that patent have the disadvantage of not having a user friendly interface for informing the user of the detection of different types of flaws and the number thereof, in order to enable the user to make decisions as to the suitability of a particular web of material.

SUMMARY OF THE INVENTION

It is an object of the present invention to provide a new and improved method and apparatus user friendly display interface for indicating the types and number of flaws during the inspection of a moving web of material and which eliminates the disadvantages of the prior art.

A further object of the present invention is to provide a flaw annunciator method and system including a display matrix which includes discrete areas, each of which corresponding to a type of flaw and each of which is capable of automatically changing color when a preselected threshold number of flaws or flaw density is detected on a moving web of material.

These and other objects and advantages of the present invention are achieved in accordance with the present invention by a flaw annunciator method and system wherein each of any of a plurality of types of flaws are detected by detecting means in a moving web and signals corresponding thereto are generated. Controllable display means comprises a matrix of areas, each area corresponding to one type of the plurality of flaws and each being capable of displaying any one of a plurality of colors. The display means are controlled on the basis of the signals from the detecting means to initially display all of the areas in a first color corresponding to an acceptable number of flaws for each type of flaw. Individual areas change their color to a second color corresponding to a caution indication to a user in response to the detection of a first preselected number of flaws of a type corresponding to that area. Individual areas change their color from the caution indicating color to a third color indicating a failure when the detecting means detects a second preselected number of flaws of a type corresponding to that area, wherein the second preselected number is greater than the first preselected number.

The display means is also capable of displaying a fourth color in each area which corresponds to an indication to the user that the flaw is repeating. This change is responsive to the detection of a preselected number flaws of each type occurring within a given time period.

In accordance with the present invention, the display means is a computer monitor which can be a color CRT display, a color LCD or a color LED display or any other type of display which is capable of displaying different colors in different areas of the display screen.

The first color is preferably green, the second color is preferably yellow, the third color is preferably red and the fourth color is preferably blue.

These and other features of the present invention will be described in more detail from the following description of preferred embodiments taken in connection with the accompanying drawings, wherein:

BRIEF DESCRIPTION OF THE DRAWINGS

FIG. 1 is a schematic representation of the system according to the present invention;

FIG. 2 is a flow chart of the system control by the computer shown in FIG. 1.

DETAILED DESCRIPTION OF THE INVENTION

Figure 3:
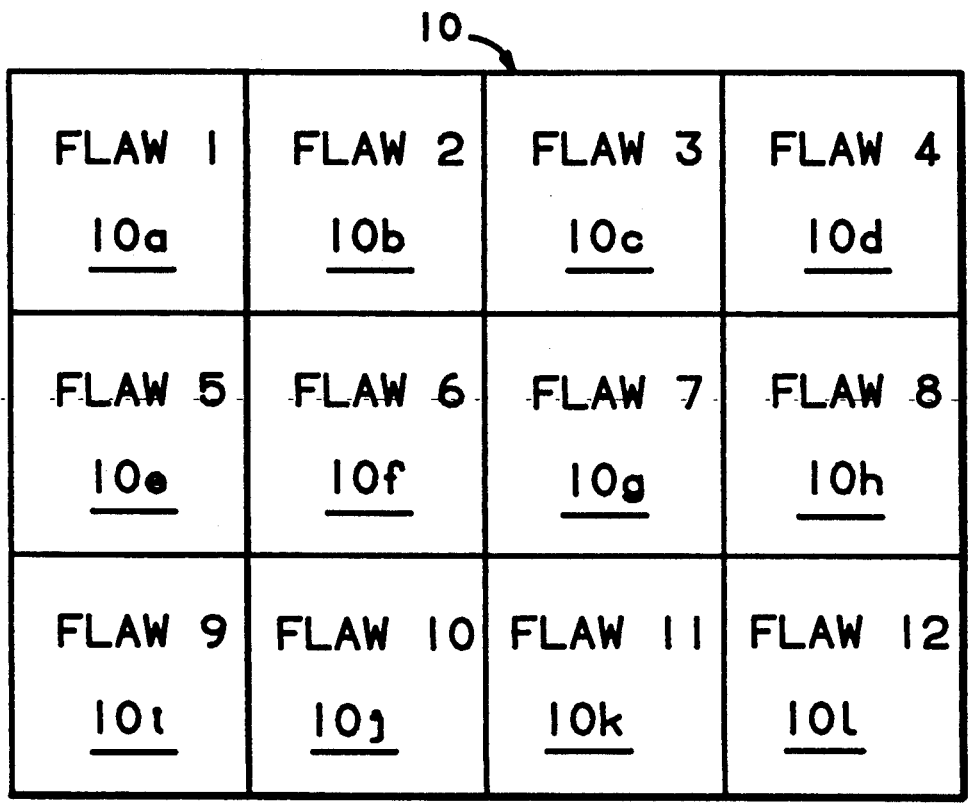
FIGS. 3, 4, 5, and 6 show different screen displays on the display 10 of FIG. 1.

In the following description, like elements will bear the same reference numerals.

Referring now to FIG. 1, a web of material W such as paper, fabric, plastic, foil, etc. is wound from a supply roll 1 to a take-up roll 2 in a direction 3. While moving, the web W is scanned by a beam of light in a direction perpendicular to the direction of movement 3 by a scanner 4 which is preferably a laser scanning flaw detection system such as that disclosed in U.S. Pat. No. 4,265,545 and incorporated hereby by reference or more preferably by the laser scanner flaw detection system disclosed in copending U.S. application Ser. No. (Intec 201), filed on the same day as this application by the same applicant and assignee and the disclosure of which is incorporated herein by reference. The light beam reflected by web W is received by detector 7 which generates signals corresponding to each of a plurality of types of flaws which are present on the moving web W. The detector can be any conventional flaw detector such as that disclosed in U.S. Pat. No. 4,265,545 or it can preferably be the detector disposed in copending U.S. application Ser. No. (Intec 202) filed on the same day as this application by the same applicant and assignee and the disclosure of which is incorporated hereby by reference.

The signals generated by detector 7 are fed to logic circuitry which is preferably in a computer 5 which is preferably an IBM PC AT computer having an 80286 or 80386 central processing unit and a CGA, EGA or VGA video adaptor board for driving a color display 10. The display 10 can be any conventional color monitor. The computer 5 is also capable of receiving inputs from a keyboard 6, which is a conventional computer keyboard.

Computer 5 is programmed to control display 10 to display a matrix of areas 10a–10l as shown in FIG. 3. Each area in the matrix is set to correspond to one of a plurality of different flaws capable of being detected by scanner 4 and detector 7. While this embodiment shows a matrix of 12 different flaws capable of being displayed, it is recognized by those skilled in the art that this system can be used to display less flaws or more flaws depending upon the scanner used and the type of material being scanned. The display 10 is capable of displaying more and differently shaped areas depending upon the type of video adapter used and the resolution of the screen.

FIG. 2 shows a flow chart of the software control of the display 10 by computer 5 during use of the system.

Initially, as set forth in block 101 the user creates definitions for 1 to 12 possible defect or flaw types that can be detected for a particular web product. These definitions are input by keyboard 6 and each flaw type 1-12 is given a name which appears in the area 10a-10l corresponding thereto where the legend "FLAW n" is now present. The user also calibrates the specific data for a particular physical flaw which corresponds to that defect type and stores this information in computer memory.

The calibration is carried out by placing a sample of the web under the scanner, the sample having the particular type of defect to be sensed. The scanner will then scan the sample and generate signals which are saved in the computer as to those corresponding to the flaw contained on the sample. Once the flaw has been defined, a preselected flaw number 1-12 and corresponding flaw area 10a-10l are linked therewith.

In step 102, the user inputs via keyboard 6 the threshold values and the density values for each flaw. For example, with respect to a defect such as a hole which is entered as flaw 1 and named "hole", the number of defects which must be counted before the area 10a turns from green (safe) to yellow (caution) is input via the keyboard 6. Similarly the value at which the number of defects will cause the display area to go from yellow to red (failure) is input and the number of defects sensed within a given time (corresponding to a given distance depending upon the web speed) is input to change the area 10a from any color to blue which usually indicates a reading error and advises the user to repeat the calibration and inspection (repeat scan).

After the setup steps 101 and 102, the scanner is started in step 103 and the computer sets all of the display areas 10a-10l to green. The detector now generates signals corresponding to detected flaws and in step 104 the computer compares the signals to the definitions for the flaws, counts the number detected flaws and compares same to the threshold and density values that have been stored therein. The computer compares the number of detected flaws for each flaw in turn and thus continuously repeats. Thus for the flaw corresponding area 10i, if in step 105, the detected densities for that flaw is above the value set for blue, then the display area 10i, is immediately set to blue in step 106. If not, the detected number of flaws is compared to the threshold value for yellow in step 107. If the value is below the threshold for yellow, then the computer starts comparing the detected number of flaws for the flaw corresponding to area 10j against the blue threshold value in step 105 and the yellow threshold value in steps 107 when the computer returns to area 10i again, it will again perform steps 105 and 107.

If the number of flaws detected should note caution to the user, then the computer changes the color of display area 10i to yellow in step 108 and thereafter in steps 109 and 111, the number of flaws are compared to the threshold for blue and the threshold for red. If the detected number is below the blue and red thresholds, then the computer performs the appropriate steps for area 10j. When the computer returns to area 10i it will perform steps 109 and 111 again. If the density is above the threshold set in step 109, the area will be set to blue in step 110. If not, the threshold with respect to red is checked in step 112 and if it is above that threshold, the display area 10i will be changed to red in step 112 signifying a failure to the user.

When the computer again returns to area 10i it continuously check to see if the threshold for blue is reached in step 113 and if so, the display area will be changed to blue in step 114. The blue setting indicates a repeating error, due to the fact that a continuing error is being found which indicates a possible error in the detection system.

The system according to the present invention visually indicates to the user by means of predetermined colors, an acceptable number of detected flaws, a cautionary number of detected flaws and a failing number of detected flaws as well as an indication that the testing should be repeated. The user need not have to perform calculations or read numbers relating to a particular type of flaw in order to determine whether a web is acceptable or whether a cautionary, a failure or a repeat warning is being given. The user need only see a change in color to recognize the fact that further attention is necessary.

A major advantage of the system accoding to the invention is that it is distance insensitive, in that a user can be at a distance from the monitor or screen, such as across the room, and need only glance at the display to see that it is all green and that there is no problems in the inspection.

In an alternative simplified embodiment, only two colors, for example, green and red, can be used with one corresponding threshold to indicate pass or fail.

Figure 4:
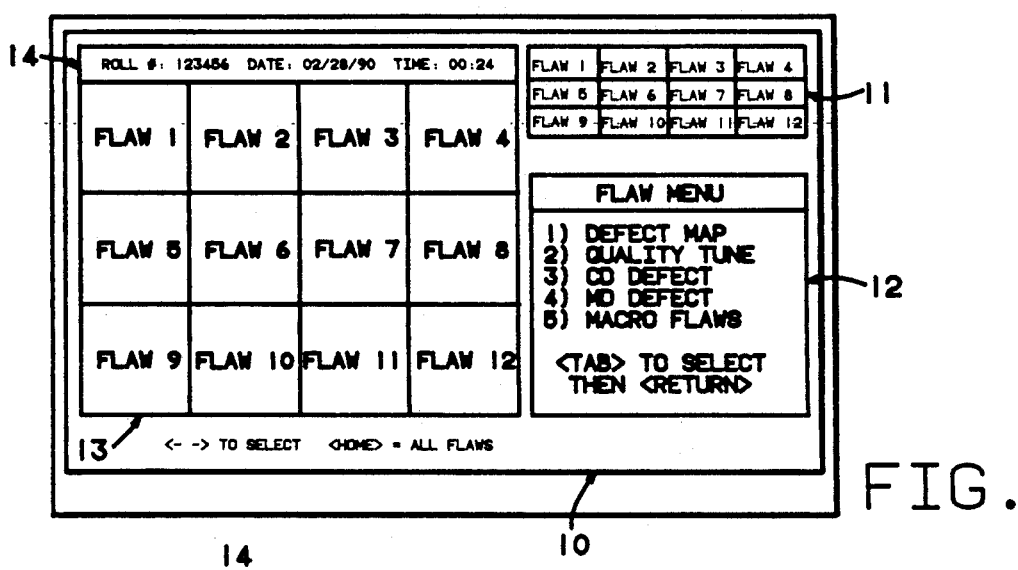

The system also enables the user to obtain further information relating to the flaws while maintaining the annunciator matrix area on the screen. This is shown in FIG. 4 wherein the computer is effective to break the screen 10 up into screen areas 11-14 to provide further information to the user. In screen area 11, the matrix is now disposed in a smaller form but having the same attributes of relative position and color capabilities. In area 12 a menu of requestable analyses to be performed is displayed for selection on the keyboard and in area 13 a selection matrix of the flaws is displayed to enable the user to select the flaw to be analyzed. Area 14 contains is information relating to the roll being scanned, the date of the scan and the time.

Figure 5:
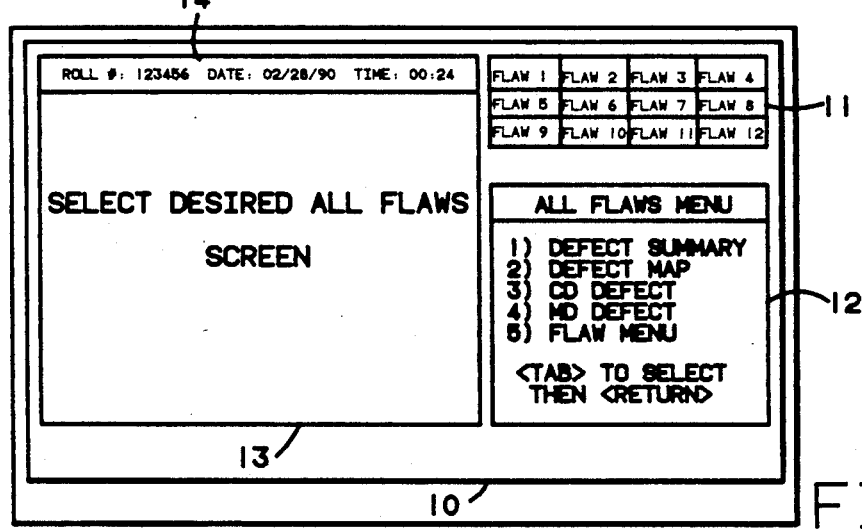
Figure 6:
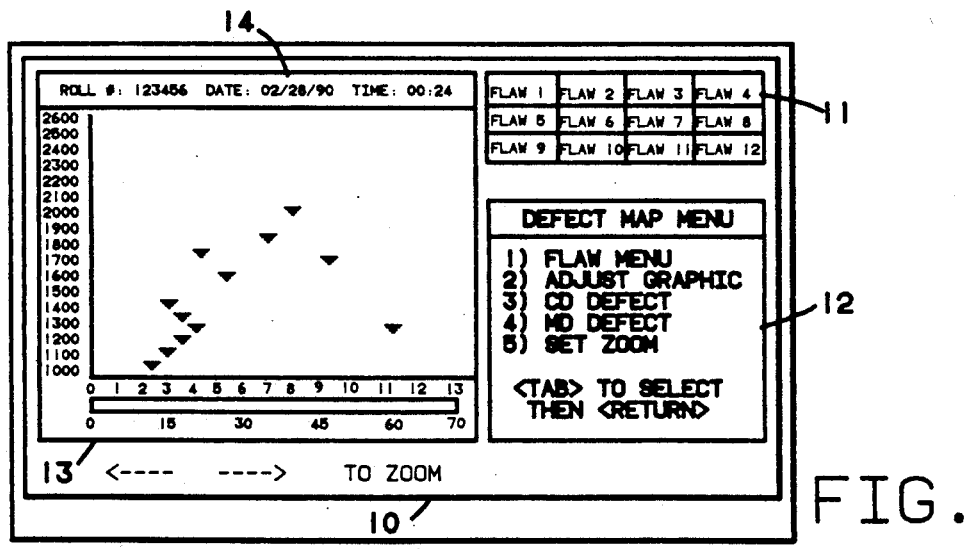

From the menu shown in FIG. 4, the user can select any one of flaws 1-12 or alternatively from the menu shown in FIG. 5, the user can select all the flaws to produce a defect map shown in FIG. 6 in area 13. The defect map is a display of the number of defects already at a particular material distance along the web for either a particularly selected flaw from the menu of FIG. 4 or of the total number of all detected flaws from the menu of FIG. 5.

Thus the user can utilize the computer to make further analyses driving the inspection without losing the annunciator type matrix display interface.

It should be clear to one skilled in the art that changes and modifications can be made to the present invention without departing form the spirit and scope of the present invention disclosed herein. For example, different colors can be used to indicate different threshold levels, and in the case of a monochromatic display, different shades or different hatching can be utilized to distinguish one threshold level from another on the display. Whereas a rectangular matrix has been illustrated herein, other shapes and configurations can be used in order to display the different flaw types and color changes to a user.

It will be appreciated that the instant specification and claims are set forth by way of illustration and not limitation, and that various modifications and changes may be made without departing from the spirit and scope of the present invention.

What is claimed is:

1. A method for detecting flaws in a moving web, comprising the steps of:
    detecting each of any of a plurality of different types of flaws in the moving web and generating signals corresponding thereto; and
    visually indicating when the detected number of flaws for any type of flaw is greater than a preselected threshold value by displaying a matrix of areas each corresponding to one type of the plurality of type of flaws, wherein each area is capable of displaying either of a first and a second color; and controlling the display for each area to initially display the area in the first color and to individually change the color of the area to the second color in response to the detection of a first preselected threshold value of detected flaws of the type corresponding to the area.

2. The method according to claim 1, wherein each area is capable of displaying any one of the first, the second and a third color; and the step of controlling the display for each area includes individually changing the color of the area from the second color to the third color in response to the detection of a second preselected threshold value of detected flaws of the type corresponding to the area, wherein the second preselected threshold value is greater than the first preselected threshold value.

3. The method according to claim 2, wherein the first color corresponds to an acceptable number of flaws for each type, the second color corresponds to a cautionary number of flaws for each type and the third color corresponds to a failing number of flaws for each type.

4. The method according to claim 1, wherein the matrix is displayed on a color monitor.

5. The method according to claim 2, further comprising displaying a fourth color in each area when a preselected threshold value of corresponding type detected flaws is detected within a given time period.

6. A flaw detection system comprising: means for detecting each of any of a plurality of different types of flaws in a moving web and for generating signals corresponding thereto; controllable display means comprising a matrix of areas each corresponding to one type of the plurality of types of flaws and each capable of displaying either of a first and a second color; and means receptive of the signals from the detecting means for controlling the display means to initially display all of the areas in the first color and to individually change the color of each area to the second color in response to a first preselected threshold value of detected flaws of the type corresponding to the area.

7. The system according to claim 6, wherein the matrix of areas are each capable of displaying any one of the first, the second and a third color and the means receptive of the signals from the detecting means for controlling the display means comprises means for individually changing the color of an area from the second color to the third color in response to a second preselected threshold value of detected flaws of the type to said area, wherein the corresponding second preselected threshold value is greater than the first preselected threshold value.

8. The system according to claim 7, wherein the first color corresponds to an acceptable number of flaws for each type, the second color corresponds to a cautionary number of flaws for each type and the third color corresponds to a failing number of flaws for each type.

9. The system according to claim 6, wherein the display means comprises a color monitor.

10. The system according to claim 7, wherein the display means has means for displaying a fourth color in each area and the controlling means has means for changing the color of each area to the fourth color when a preselected threshold value of corresponding type flaws is detected within a given time period.

* * * * *